(12) United States Patent
Smullin et al.

(10) Patent No.: US 11,931,288 B2
(45) Date of Patent: Mar. 19, 2024

(54) COLLAPSIBLE INTRAVAGINAL CUPS

(71) Applicants: Carolyn P. Smullin, Los Angeles, CA (US); Abhishek Venkataramana, Los Angeles, CA (US); Jocelyn Finger, Los Angeles, CA (US); Maneesha Thaker, Los Angeles, CA (US); Ming-Yeah Hu, Los Angeles, CA (US); Sirilasya Rallabhandi, Upland, CA (US); Supreethi Penmetcha, Mountain View, CA (US)

(72) Inventors: Carolyn P. Smullin, Los Angeles, CA (US); Abhishek Venkataramana, Los Angeles, CA (US); Jocelyn Finger, Los Angeles, CA (US); Maneesha Thaker, Los Angeles, CA (US); Ming-Yeah Hu, Los Angeles, CA (US); Sirilasya Rallabhandi, Upland, CA (US); Supreethi Penmetcha, Mountain View, CA (US)

(*) Notice: Subject to any disclaimer, the term of this patent is extended or adjusted under 35 U.S.C. 154(b) by 334 days.

(21) Appl. No.: 17/326,773

(22) Filed: May 21, 2021

(65) Prior Publication Data
US 2022/0370239 A1    Nov. 24, 2022

(51) Int. Cl.
*A61F 5/455* (2006.01)
*A61F 5/44* (2006.01)

(52) U.S. Cl.
CPC ............. *A61F 5/4553* (2013.01); *A61F 5/44* (2013.01); *A61F 5/455* (2013.01)

(58) Field of Classification Search
CPC ....... A61F 5/4553; A61F 5/455; A61F 5/4404
See application file for complete search history.

(56) References Cited

U.S. PATENT DOCUMENTS

| | | | | | |
|---|---|---|---|---|---|
| 1,891,761 | A | * | 12/1932 | Goodard | A61F 5/4553 |
| | | | | | 604/330 |
| 1,996,242 | A | * | 4/1935 | Hagedorn | A61F 5/4553 |
| | | | | | 604/330 |
| 2,089,113 | A | * | 8/1937 | Chalmers | A61F 5/4553 |
| | | | | | D24/141 |
| 2,234,495 | A | | 3/1941 | Lay | |
| 2,321,340 | A | * | 6/1943 | Waterbury | B29C 70/70 |
| | | | | | 264/294 |
| 2,534,900 | A | * | 12/1950 | Chalmers | A61F 5/4553 |
| | | | | | 604/330 |
| 2,613,670 | A | * | 10/1952 | Sokolik | A61F 5/4553 |
| | | | | | 128/834 |
| 2,616,426 | A | * | 11/1952 | Gordon | A61F 5/4553 |
| | | | | | 604/330 |
| 2,836,177 | A | * | 5/1958 | Sells | A61F 6/08 |
| | | | | | 128/837 |

(Continued)

*Primary Examiner* — Guy K Townsend
(74) *Attorney, Agent, or Firm* — UCLA Patent Law Clinic

(57) ABSTRACT

Systems and methods for collapsible intravaginal cup in accordance with embodiments of the invention are disclosed. In one embodiment, provided herein are devices and methods for an intravaginal insert device for collecting menstrual fluid comprising a receptacle comprising a top rim, a base, and a wall connecting the base to the top rim, wherein the top rim comprises an opening, and a ring support connected to the top rim and having an outer perimeter that is larger by at least 10% than an outer perimeter of the top rim.

17 Claims, 7 Drawing Sheets

(56) References Cited

U.S. PATENT DOCUMENTS

| | | | | |
|---|---|---|---|---|
| 3,128,767 A * | 4/1964 | Nolan | A61F 6/08 | 604/330 |
| 3,371,664 A * | 3/1968 | Pleshette | A61F 6/08 | 128/837 |
| 3,404,682 A * | 10/1968 | Waldron | A61F 13/26 | 128/838 |
| 3,626,942 A * | 12/1971 | Waldron | A61F 6/08 | 604/330 |
| 3,841,333 A * | 10/1974 | Zalucki | A61F 5/4553 | 604/330 |
| 3,845,766 A * | 11/1974 | Zoller | A61F 5/4553 | D24/141 |
| 4,031,886 A * | 6/1977 | Morhenn | A61F 2/005 | 128/837 |
| 4,381,771 A * | 5/1983 | Gabbay | A61F 6/08 | 128/836 |
| 4,703,752 A * | 11/1987 | Gabbay | A61F 6/08 | 128/841 |
| 4,799,929 A * | 1/1989 | Knowles | A61F 5/4553 | 604/331 |
| 4,848,363 A * | 7/1989 | Cattanach | A61F 5/4553 | 128/834 |
| 4,895,170 A * | 1/1990 | Tlapek | A61F 6/08 | 128/832 |
| 4,961,436 A * | 10/1990 | Koch | A61F 6/08 | 128/834 |
| D323,212 S * | 1/1992 | Crawford | D24/141 | |
| 5,207,232 A * | 5/1993 | Shihata | A61F 6/08 | 128/838 |
| 5,243,712 A * | 9/1993 | Cross | A61F 5/4556 | 4/144.2 |
| 5,295,984 A * | 3/1994 | Contente | A61F 5/4553 | 604/327 |
| 5,605,161 A * | 2/1997 | Cross | A61B 10/007 | 600/580 |
| 5,771,900 A * | 6/1998 | Austin | A61F 6/08 | 128/830 |
| 5,827,248 A * | 10/1998 | Crawford | A61F 5/4553 | 604/328 |
| 5,928,249 A * | 7/1999 | Saadat | A61B 17/42 | 606/119 |
| 5,947,992 A * | 9/1999 | Zadini | A61F 5/4553 | 606/191 |
| 6,126,616 A * | 10/2000 | Sanyal | A61B 10/0291 | 128/834 |
| 6,168,609 B1 * | 1/2001 | Kamen | A61F 5/4553 | 600/573 |
| 6,241,846 B1 * | 6/2001 | Contente | B29C 66/114 | 156/379 |
| 6,264,638 B1 * | 7/2001 | Contente | A61M 31/002 | 604/285 |
| 6,332,878 B1 * | 12/2001 | Wray | A61F 5/4556 | 128/830 |
| 6,796,973 B1 * | 9/2004 | Contente | A61F 5/4553 | 128/832 |
| 7,845,355 B2 * | 12/2010 | Moench | A61F 6/08 | 128/833 |
| 8,454,493 B2 * | 6/2013 | La Vean | A61F 6/08 | 600/33 |
| 8,690,847 B2 * | 4/2014 | Norman | A61F 5/4553 | 604/327 |
| 8,795,248 B2 * | 8/2014 | Shihata | A61F 5/4553 | 604/385.18 |
| 9,357,982 B2 * | 6/2016 | Edmunds | A61F 13/2045 | |
| 10,016,308 B2 * | 7/2018 | Knox | A61F 13/00085 | |
| 10,188,543 B2 * | 1/2019 | Lin | A61F 5/4405 | |
| D852,361 S * | 6/2019 | Sedic | D24/141 | |
| D852,362 S * | 6/2019 | Sedic | D24/141 | |
| 10,357,395 B2 * | 7/2019 | Miller | A61F 5/4404 | |
| D864,390 S * | 10/2019 | Sedic | D24/141 | |
| D892,324 S * | 8/2020 | Yi | D24/141 | |
| D894,386 S * | 8/2020 | LeClerc | D24/141 | |
| D895,798 S * | 9/2020 | Newman | D24/141 | |
| D895,799 S * | 9/2020 | Newman | D24/141 | |
| D895,800 S * | 9/2020 | Knox | D24/141 | |
| 10,888,450 B2 * | 1/2021 | Sedic | A61F 5/4553 | |
| 10,893,975 B2 * | 1/2021 | Sedic | A61F 5/4553 | |
| 10,959,873 B2 * | 3/2021 | Wilson | A61F 5/4553 | |
| 10,973,496 B2 * | 4/2021 | Naseri | A61F 13/535 | |
| D923,785 S * | 6/2021 | Tsai | D24/141 | |
| 11,219,548 B2 * | 1/2022 | Conti | A61F 6/12 | |
| 11,534,329 B1 * | 12/2022 | Thornton | A61F 5/4404 | |
| 11,583,433 B2 * | 2/2023 | Brush | A61F 5/4404 | |
| 2007/0289598 A1 * | 12/2007 | LaBarre | A61F 6/08 | 128/837 |
| 2008/0077097 A1 * | 3/2008 | Chambers | A61F 5/4553 | 604/330 |
| 2008/0200888 A1 * | 8/2008 | Gooch | A61F 5/4553 | 604/330 |
| 2010/0242968 A1 * | 9/2010 | Vean | A61F 6/08 | 128/830 |
| 2010/0312204 A1 * | 12/2010 | Sheu | A61F 5/4408 | 604/330 |
| 2013/0110060 A1 * | 5/2013 | Shihata | A61F 5/4553 | 604/330 |
| 2013/0237771 A1 | 9/2013 | Runkewitz et al. | | |
| 2014/0012216 A1 * | 1/2014 | Shaviv | A61F 5/4553 | 29/428 |
| 2015/0164680 A1 * | 6/2015 | Chen | A61F 13/8405 | 604/359 |
| 2016/0278988 A1 * | 9/2016 | Knox | A61F 15/005 | |
| 2017/0189222 A1 * | 7/2017 | Lin | A61F 5/4553 | |
| 2017/0360594 A1 * | 12/2017 | Park | A61F 5/449 | |
| 2018/0028350 A1 * | 2/2018 | Wilson | A61F 5/4553 | |
| 2018/0140458 A1 * | 5/2018 | Brockway | A61F 5/4553 | |
| 2018/0199874 A1 * | 7/2018 | Hwang | A61B 5/150862 | |
| 2018/0214298 A1 * | 8/2018 | Medas | A61F 5/4553 | |
| 2019/0000680 A1 | 1/2019 | Deoliveira et al. | | |
| 2019/0021898 A1 * | 1/2019 | Ahn | A61F 5/4553 | |
| 2019/0083296 A1 * | 3/2019 | Miller | A61F 5/4553 | |
| 2019/0099166 A1 * | 4/2019 | Naseri | A61F 13/15 | |
| 2019/0192335 A1 * | 6/2019 | Sedic | A61F 5/4553 | |
| 2019/0201231 A1 * | 7/2019 | Sedic | A61F 5/4553 | |
| 2019/0282350 A1 * | 9/2019 | Conti | A61F 2/0095 | |
| 2019/0314191 A1 * | 10/2019 | Bobarikin | A61F 5/4553 | |
| 2019/0336318 A1 * | 11/2019 | Kubo | A61F 5/455 | |
| 2019/0358077 A1 * | 11/2019 | Bauer | A61F 5/4553 | |
| 2020/0022835 A1 * | 1/2020 | Lloveras Macià | A61F 5/4553 | |
| 2020/0046572 A1 * | 2/2020 | Hwang | A61F 5/4404 | |
| 2020/0078208 A1 * | 3/2020 | Stoebe-Latham | A61F 5/4553 | |
| 2020/0078209 A1 * | 3/2020 | Stoebe-Latham | A61F 13/55105 | |
| 2020/0179157 A1 * | 6/2020 | Pitacco | A61F 5/44 | |
| 2020/0206019 A1 * | 7/2020 | Brown | A61F 5/4553 | |
| 2020/0214876 A1 * | 7/2020 | Tsai | A61F 5/4553 | |
| 2020/0375788 A1 * | 12/2020 | Zhang | A61F 5/4553 | |
| 2021/0113363 A1 * | 4/2021 | Evans | A61F 5/4553 | |
| 2021/0128342 A1 * | 5/2021 | Miller | A61F 5/455 | |
| 2021/0251815 A1 * | 8/2021 | Brown | A61F 13/2045 | |
| 2021/0353473 A1 * | 11/2021 | Yi | A61F 5/4553 | |
| 2021/0378880 A1 * | 12/2021 | Nur | A61L 15/18 | |
| 2022/0331146 A1 * | 10/2022 | Brush | A61F 5/4553 | |
| 2022/0331147 A1 * | 10/2022 | Brush | A61F 5/4553 | |

* cited by examiner

COLLAPSIBLE INTRAVAGINAL CUPS

FIELD OF THE INVENTION

The present invention generally relates to intravaginal devices and more specifically to intravaginal menstrual cups that are collapsible.

BACKGROUND

Menstrual cups are menstrual hygiene devices placed intravaginally in the vaginal canal to collect menstrual fluids and avoid leakage of menstrual fluids from the vagina. However, menstrual cups may not work effectively for women who experience laxity of the pelvic floor and vaginal tissues, organ prolapse, or urinary and/or fecal incontinence. The ineffectiveness of menstrual cups in such women may be due to reduced suction or inability to create suction to seal the menstrual cup in place in the vaginal canal.

SUMMARY OF THE INVENTION

The various embodiments of the present collapsible intravaginal cups contain several features, no single one of which is solely responsible for their desirable attributes. Without limiting the scope of the present embodiments, their more prominent features will now be discussed below. In particular, the present collapsible intravaginal cups will be discussed in the context of collecting menstrual fluids and alleviating symptoms of urinary or fecal incontinence or organ prolapse. However, the use of collapsible intravaginal cups is merely exemplary and various other collapsible intravaginal cups may be utilized for collecting menstrual fluids and alleviating incontinence or organ prolapse as appropriate to the requirements of a specific application in accordance with various embodiments of the invention. After considering this discussion, and particularly after reading the section entitled "Detailed Description," one will understand how the features of the present embodiments provide the advantages described here.

In a first aspect, an intravaginal insert device for collecting menstrual fluid is provided, the intravaginal insert device comprising a receptacle comprising a top rim, a base, and a wall connecting the base to the top rim, wherein the top rim comprises an opening, and a ring support connected to the top rim and having an outer perimeter that is larger by at least 10% than an outer perimeter of the top rim.

In an embodiment of the first aspect, the ring support has a width larger than a thickness of the wall of the receptacle.

In some embodiments of the first aspect, the ring support has a width of at least 5 mm and no more than 50 mm.

In some embodiments of the first aspect, the ring support comprises one or more flexible areas that is more flexible than rest of the ring support.

In some embodiments of the first aspect, the ring support is configured to be bendable at the one or more flexible areas.

In some embodiments of the first aspect, the ring support comprises one or more flexible areas having a higher elasticity than rest of the ring support.

In some embodiments of the first aspect, the outer perimeter of the ring support is configured to apply pressure to a vaginal wall once inserted into a vaginal canal.

In some embodiments of the first aspect, the outer perimeter of the ring support is configured to distend a vaginal wall once inserted into a vaginal canal.

In some embodiments of the first aspect, the receptacle tapers from the top rim to the base, and wherein the outer perimeter of the top rim is greater than an outer of the base.

In some embodiments of the first aspect, the device comprises a biocompatible elastomeric polymer.

In some embodiments of the first aspect, the biocompatible polymer comprises a medical grade silicone.

In some embodiments of the first aspect, the receptacle is configured to fold lengthwise along an axis running from the top rim to the base.

In some embodiments of the first aspect, the wall of the receptacle comprises two or more foldable areas, wherein each of the two or more foldable areas comprise a notched circumference along the wall that is substantially parallel to the top rim.

In some embodiments of the first aspect, the two or more foldable areas are spaced at least 1 mm apart from each other.

In some embodiments of the first aspect, a first notched circumference of a first of the two or more foldable areas is notched on an outer surface of the wall and a second notched circumference of a second of the two or more foldable areas is notched on an inner surface the wall.

In some embodiments of the first aspect, the two or more foldable areas are configured to fold the wall of the receptacle in alternating directions.

In some embodiments of the first aspect, the wall of the receptacle is collapsible.

In some embodiments of the first aspect, the wall of the receptacle has a height that is no more than a height of the ring support when the wall is collapsed.

In some embodiments of the first aspect, the wall of the receptacle comprises an outward surface comprising a surface texture, wherein the surface texture is configured to provide improved grip.

In some embodiments of the first aspect, the wall of the receptacle comprises an outward surface comprising one or more outward protrusions, wherein the one or more outward protrusions are configured to provide improved grip.

BRIEF DESCRIPTION OF THE DRAWINGS

The various embodiments of the present collapsible intravaginal cup now will be discussed in detail with an emphasis on highlighting the advantageous features. These embodiments depict the novel and non-obvious collapsible intravaginal cup shown in the accompanying drawings, which are for illustrative purposes only. These drawings include the following figures.

DETAILED DESCRIPTION OF THE DRAWINGS

Figure 1:
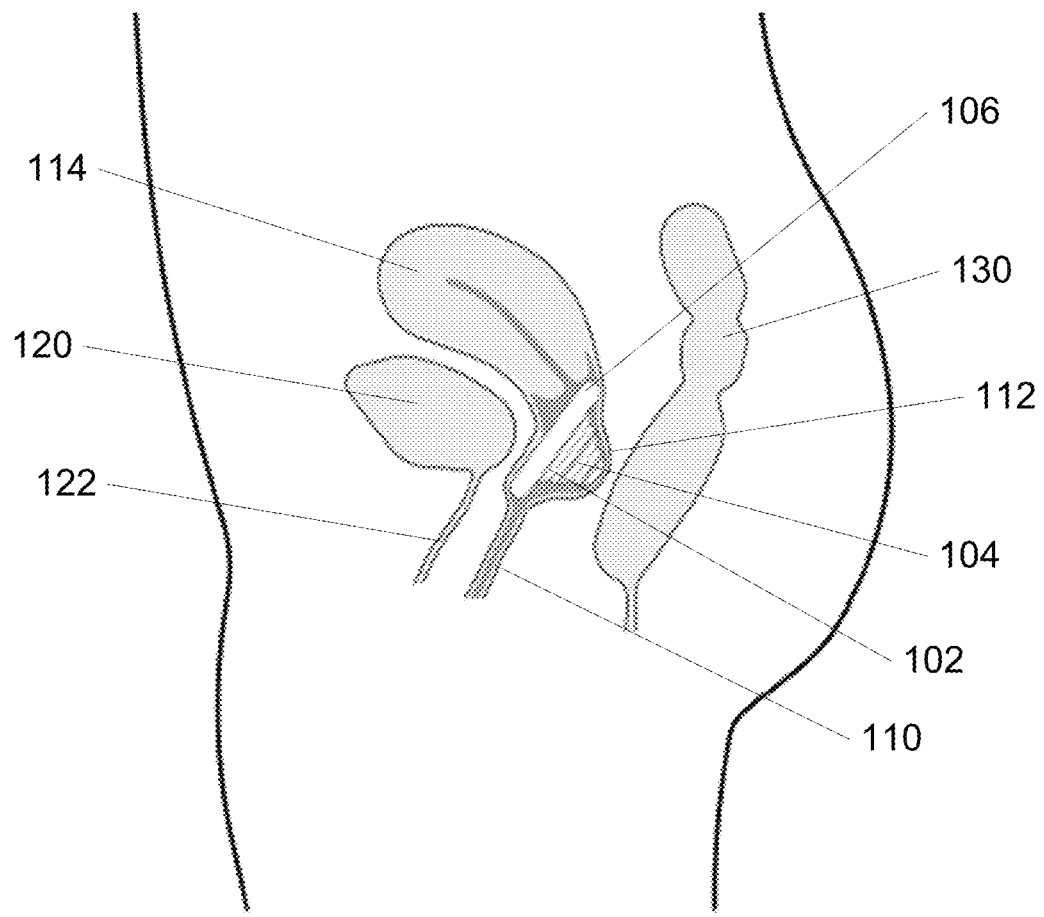
FIG. 1 shows an exemplary embodiment of an intravaginal insert device placed in the vaginal canal in the body of a user.

The following detailed description describes the present embodiments with reference to the drawings. In the drawings, reference numbers label elements of the present embodiments. These reference numbers are reproduced below in connection with the discussion of the corresponding drawing features.

One aspect of the present embodiments includes the realization that many menstrual cups do not address the menstrual and pelvic floor needs of women who experience laxity in the pelvic floor or gynecological tissues. The tissue laxity may develop due to a variety of factors, including but not limited to, advanced age, genetic predisposition, and history of pregnancy and/or childbirth. This population represents an enormous number of women who are unable to use menstrual cups as the laxity in the vaginal tissue or prolapsed pelvic organs may not allow them to create and maintain the suction seal of the menstrual cup to the wall of the vaginal canal. In such cases, the menstrual cup may fall out of or down the vaginal canal to the level of the introitus. In some cases, the menstrual cup may shift and move with activity or exercise by the user instead of staying in place as intended, which may result in discomfort for the user. In some cases, a stem at the most inferior portion of the device of the menstrual cup to facilitate removal of the menstrual cup may create discomfort from poking and chafing in women with laxity of their vaginal and pelvic tissues.

In some cases, menstrual cups may have several disadvantages in their use. In some cases, menstrual cups may be made of polyethylene, which cannot be boiled for sterilization, or of natural latex, which many users are allergic to. In some cases, menstrual cups may fail to maintain correct placement within the vagina, particularly in users with pelvic genital organ prolapse (POP) or weakened pelvic floor musculature. Generally, menstrual cups may not provide much support to the pelvic floor, particularly for users with POP or weakened pelvic floor musculature. In some cases, menstrual cups may be difficult to insert and remove. Usually, menstrual cups may rely on folding to insert the cup through the vaginal introitus, which is relatively small compared to the lumen of the vaginal canal. In some cases, this may be a steep learning curve for new users that may discourage continued use. In some cases, the cup may inadvertently expand before the cup has reached the larger lumen of the vaginal canal, which may be painful or uncomfortable. In some cases, removal of the cup may be difficult as the large diameter of the cup may be squeezed down to fit through the introitus.

In some instances, vaginal pessaries may be placed into the vaginal fornix and provide support to the vaginal walls and musculature. In some instances, the pessaries may be used to treat POP and urinary distress, including stress urinary incontinence (SUI). While presenting low risk and a high level of efficacy, pessaries may not be used concordantly with an intravaginal menstrual hygiene product, such as a menstrual cup. Often, pessaries may require fitting by a licensed healthcare provider. As such, an intravaginal device that functions similarly to a pessary that is non-absorbent, affordable, accessible, comfortable, easy for a user to self-fit, insert and remove, and be capable of collecting menstrual fluids would be beneficial.

Turning now to the drawings, provided herein are devices and methods for collecting menstrual fluids in women experiencing pelvic floor laxity, organ prolapse, or urinary and/or fecal incontinence with an intravaginal device. The devices and methods provided herein allow for collection of menstrual fluid even without forming a fluid seal with the walls of the vaginal canal that is often difficult for women experiencing laxity with tissues and organs in the pelvic floor. Often, these devices may also alleviate symptoms of pelvic floor laxity, organ prolapse, or urinary and/or fecal incontinence in the user from the pressure exerted on the vaginal wall by the ring support that has a larger perimeter than the receptacle of the intravaginal cup. The capability of the intravaginal cup to collapse into a flat structure allows for the device to be easily transportable and accessible by the user when they are ready to use the device. In some cases, the capability of the intravaginal cup to collapse into a flat structure allows the device to become flush to the ring.

Described herein are intravaginal cup devices and methods of making and using such devices by users suffering from pelvic floor laxity, organ prolapse, or urinary and/or fecal incontinence. In many embodiments, intravaginal cup devices may comprise a ring structure that stretches the wall of the vaginal canal outwardly with its larger perimeter than a receptacle of the intravaginal cup device. The distension of the vaginal canal may help to provide pelvic floor support, reduce or prevent symptoms of pelvic organ prolapse, including but not limited to, rectocele, cystocele, enterocele, and uterine prolapse, and reduce or prevent symptoms of urinary and/or fecal incontinence. Once inserted into the vaginal canal by the user, the ring support of intravaginal cup devices may provide pressure to tissues suffering from laxity and hold the lax tissues into place. In some instances, reducing movement of lax tissues, including but not limited to, rectum, anus, urethra, ureter, and bladder, may decrease incontinence events. In some instances, the ring support may help prevent prolapse of the uterus, bladder, rectum, or a combination thereof through the vaginal opening.

Described herein are intravaginal cup devices and methods of making and using such devices to improve collection of menstrual fluids in users experiencing pelvic floor laxity, organ prolapse, or urinary and/or fecal incontinence. Often, the distension of the vaginal canal by the ring support may provide a seal between the intravaginal cup and the vaginal canal even when the user is moving, coughing, sneezing, laughing, exercising, or performing activities that may increase intra-abdominal pressure or exacerbate incontinence or pelvic floor tissue issues. In various embodiments, such seals may facilitate collection and retention of the menstrual fluids and reduce leakage of menstrual fluids from the vaginal canal while the intravaginal cup is in place in the vaginal canal in the user.

There are a number of advantages provided by the intravaginal cup devices described herein. In some cases, the intravaginal cup devices may be made of hypoallergenic medical grade silicone that may allow for boiling of the device and reduce the risk for allergic reactions. In some cases, the intravaginal cup devices may provide support to the pelvic floor to alleviate symptoms of POP or other pelvic floor disorders or weaknesses. In some cases, the design of the intravaginal cup device may allow the device to maintain its position within the vaginal canal of the user during activities that increase intra-abdominal pressure, including but not limited to coughing, sneezing, laughing, and exercising. In some cases, the intravaginal cup devices may reliably collect menstrual fluid with minimal leakage while providing pelvic floor support. In some cases, the use of the intravaginal cup devices may eliminate the need for a separate standalone pessary device. In some cases, the design of the intravaginal cup device may allow for easy insertion and removal from the vaginal canal by the user. Collapsible intravaginal cups in accordance with embodiments of the invention are further discussed below.

Intravaginal Cup Devices

Provided herein are intravaginal cup devices, also referred herein as intravaginal insert devices, intravaginal support devices, or intravaginal devices, comprising a receptacle having a built-in ring structure. The intravaginal cup devices may collect intravaginal fluid and provide support for the tissues and organs in a user's pelvic floor to reduce symptoms of pelvic organ prolapse and urinary and/or fecal incontinence. Usually, the intravaginal cup devices may simultaneously function as a pelvic floor/organ support device and a menstrual fluid collection device.

An exemplary embodiment of the intravaginal cup device 102 placed in the vaginal canal 110 in the body of a user is shown in FIG. 1. The user may have a bladder 120 connected to a pair of urethras 122 as a part of their urinary system. Posterior to the urinary system, the user may have a uterus 114 which opens to a vaginal canal 110. When the intravaginal cup device 102 is in place in the vaginal canal 110 of the vagina, the vaginal canal may be distended 112 by the ring support 106, as further described below. Intravaginal fluids, such as menstrual fluids, may be collected into the receptable 104 of the intravaginal cup device 102 when the intravaginal cup device 102 is in place in the vaginal canal 110. Posterior to the vagina, the user may have a colon 130 which may be used for bowel movement. Sometimes, an individual may experience a dysfunction of one of more of the organs, including but not limited to the bladder 120, urethras 122, colon 130, rectum, or anus, resulting in urinary or fecal incontinence. Often, the intravaginal cup device 102 may be used in the vaginal fornix.

In some cases, the incontinence may be due to laxity of one or more of these organs or the supporting tissues around these organs. In some cases, providing a mechanical tension around the lax tissue may help improve or reduce symptoms of urinary or fecal incontinence. In some cases, the tissues in pelvic floor may become lax, resulting in prolapse of one or more organs in the pelvic space, including but not limited to the vagina, uterus, rectum, or colon. In some cases, providing a mechanical tension to help support the prolapsing organ may improve the discomfort, pain, and/or symptoms of organ prolapse. In some cases, women may experience pelvic organ prolapse and urinary and/or fecal incontinence more commonly after a pregnancy. In some cases, women may experience pelvic organ prolapse and urinary and/or fecal incontinence more commonly after a vaginal delivery. Although specific collapsible intravaginal cup devices for collecting menstrual fluids are discussed above with respect to FIG. 1, any of a variety of intravaginal cup devices as appropriate to the requirements for collecting intravaginal fluids or providing support to the pelvic organs may be utilized in accordance with embodiments of the invention. Open configurations of collapsible intravaginal cups in accordance with embodiments of the invention are further discussed below.

Open Configuration of Intravaginal Cup Devices

Figure 2:
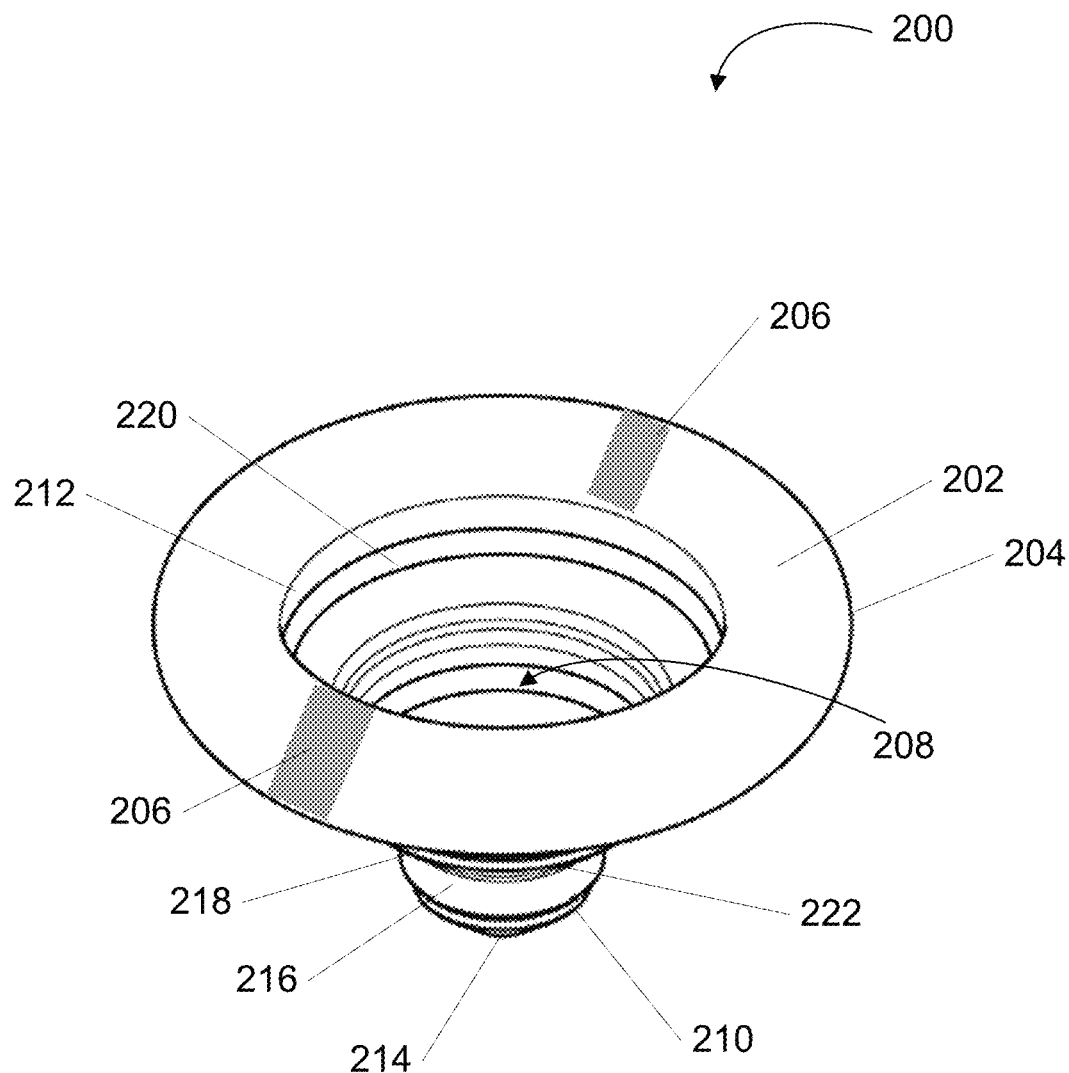
FIG. 2 shows a top front perspective view of an intravaginal insert device in an open configuration in accordance with an embodiment of the invention.
Figure 3:
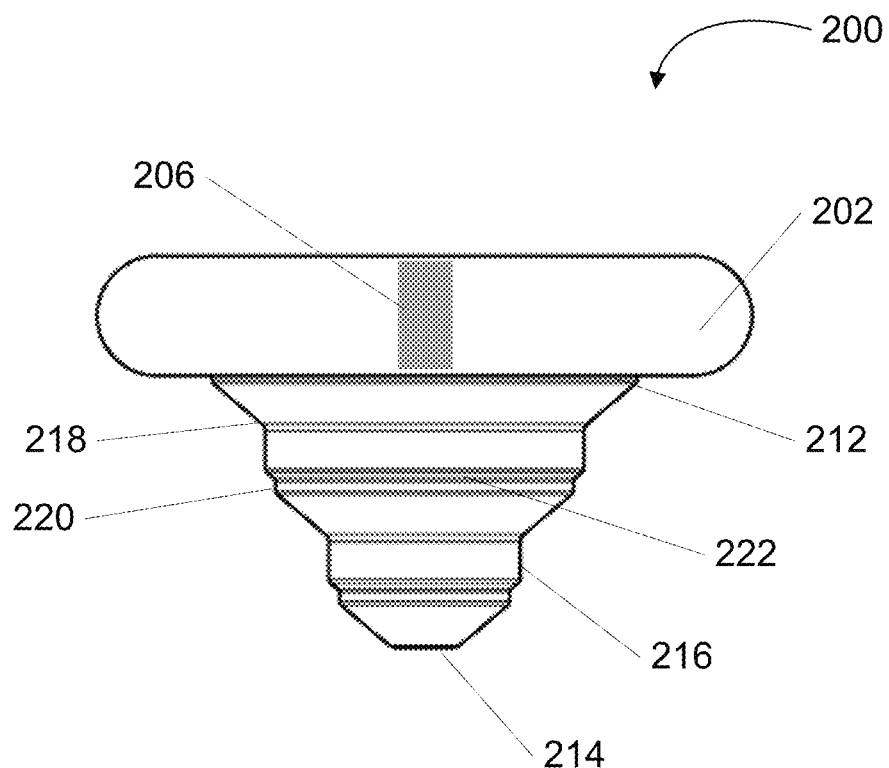
FIG. 3 shows a side view of an intravaginal insert device an open configuration in accordance with an embodiment of the invention.
Figure 4:
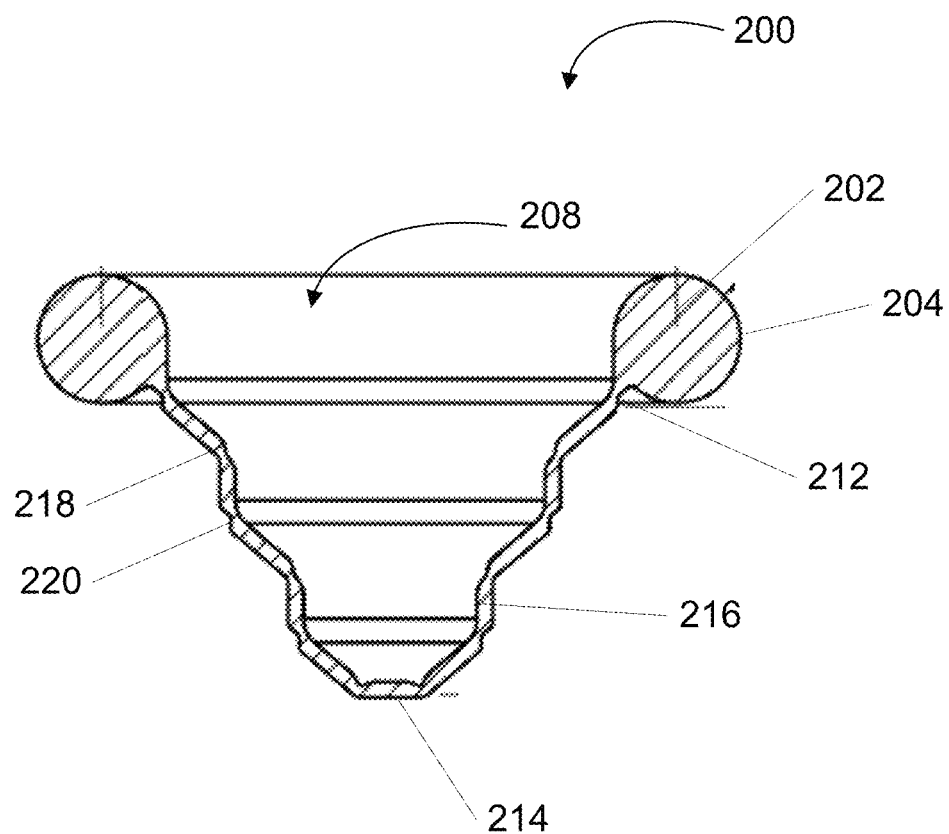
FIG. 4 shows a cross-sectional view of an intravaginal insert device an open configuration in accordance with an embodiment of the invention.

Various views of the intravaginal cup device in an open configuration are shown in FIGS. 2-4. FIG. 2 shows a top front perspective view, FIG. 3 shows a side view, and FIG. 4 shows a cross-sectional view of the intravaginal device 200 an open configuration. In some embodiments, the intravaginal device 200 comprises a ring support 202 and a receptacle 210. In some embodiments, the ring support 202 may include an outer perimeter 204. In some embodiments, the ring support 202 comprises one or more flexible areas 206 that is more flexible than the rest of the ring support. In some embodiments, the ring support 202 is configured to be bendable at the one or more flexible areas 206. In some embodiments, the one or more flexible areas 206 allow the ring support 202 to bend when a force is applied to the ring support 202. In some embodiments, the one or more flexible areas 206 has a higher elasticity than the rest of the ring support 202. In some embodiments, the bendable flexible areas of the ring support facilitate insertion of the intravaginal device through the opening of the vaginal canal and into the vaginal canal of the user by allowing the ring support to bend or flex. In some embodiments, the receptacle 210 comprises a top rim 212, a base 214, and a wall 216 connecting the base 214 to the top rim 212. In some embodiments, the outer perimeter 204 may be larger by at least 10% than an outer perimeter of the top rim 212. In some embodiments, the top rim 212 comprises an opening 208. In some embodiments, the ring support 202 has a width larger than a thickness of the wall 216 of the receptacle 210. In some embodiments, the wall 216 of the receptacle 210 comprises two or more foldable areas 218, 220. In some embodiments, each of the two or more foldable areas 218, 220 comprises a notched circumference 222 along the wall that is substantially parallel to the top rim. Although open configurations of the collapsible intravaginal cup devices and their uses for collecting menstrual fluids are discussed above with respect to FIGS. 2-4, any of a variety of intravaginal cup devices having various open configurations as appropriate to the requirements for collecting intravaginal fluids or providing support to the pelvic organs may be utilized in accordance with embodiments of the invention. Closed configurations of collapsible intravaginal cups in accordance with embodiments of the invention are discussed further below.

Collapsed Configuration of Intravaginal Cup Devices

Figure 5:
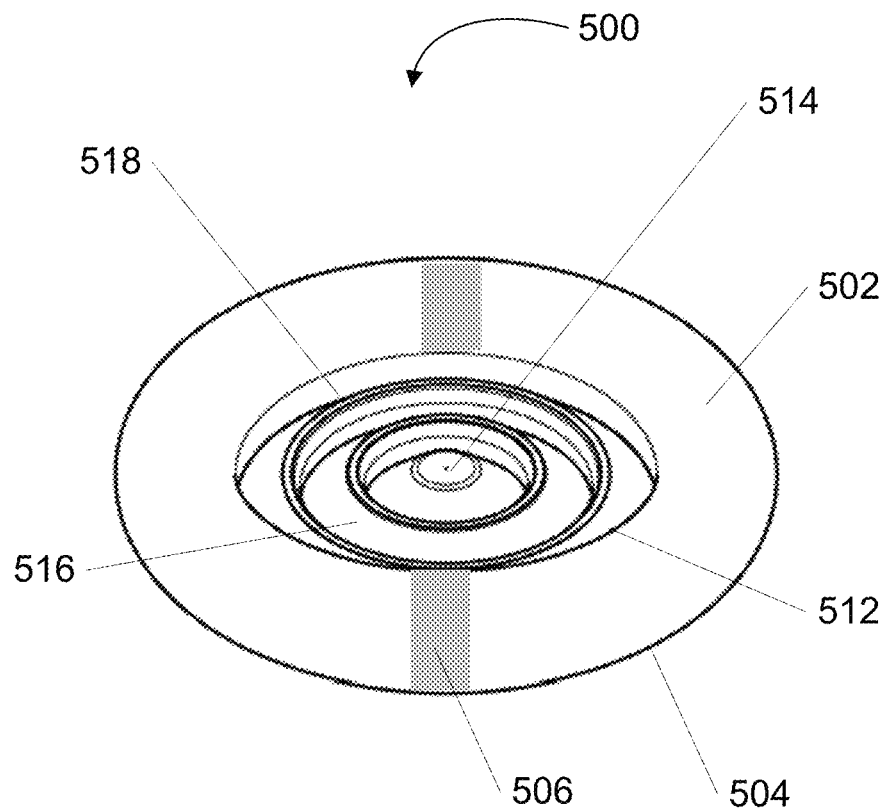
FIG. 5 shows a top front perspective view of an intravaginal insert device in a collapsed configuration in accordance with an embodiment of the invention.
Figure 6:
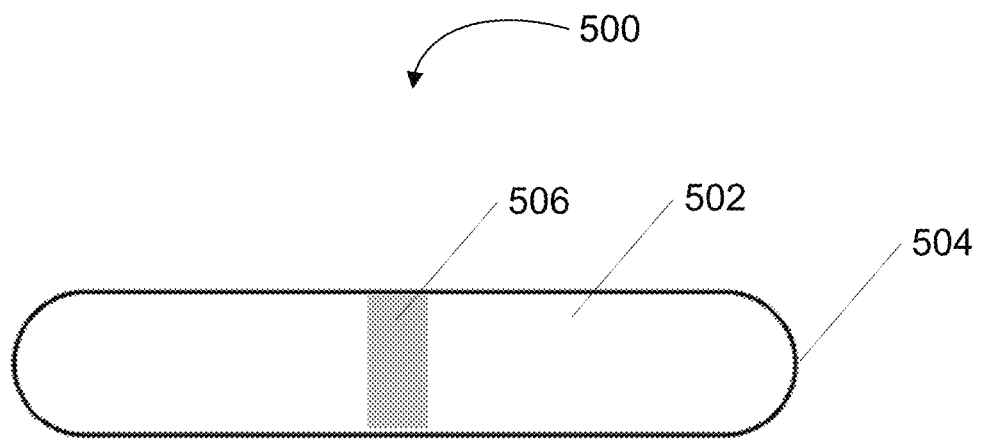
FIG. 6 shows a side view of an intravaginal insert device in a collapsed configuration in accordance with an embodiment of the invention.
Figure 7:
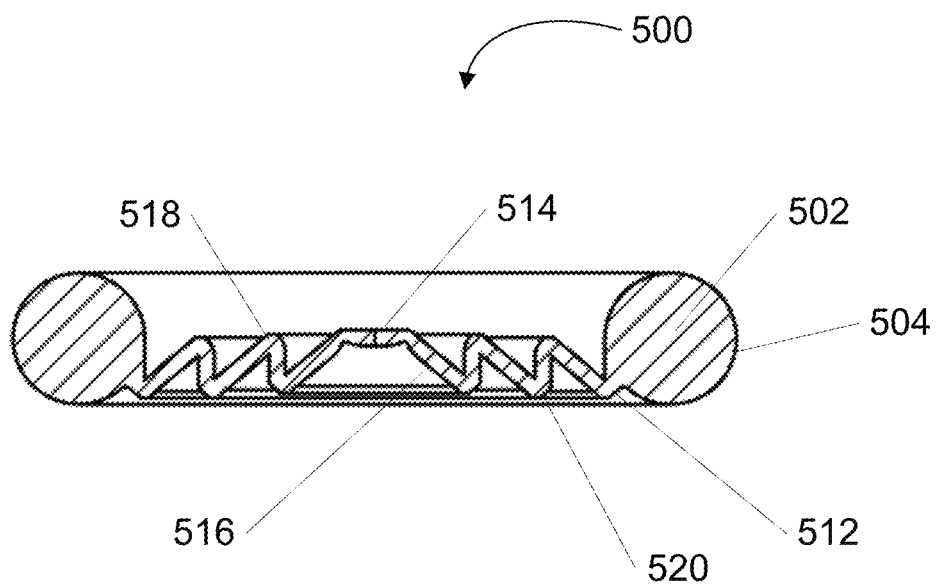
FIG. 7 shows a cross-sectional view of an intravaginal insert device in a collapsed configuration in accordance with an embodiment of the invention.

In some embodiments, the receptacle of the intravaginal cup devices may be collapsible to become flush with the ring support structure. Such collapsed intravaginal devices may make it easier for the device to be portable by the user. In some embodiments, the collapsed intravaginal devices may function to provide pelvic floor support and may collect little to no fluids when the collapsed intravaginal device is placed into the vaginal canal of a user. Various views of the intravaginal cup device in a collapsed configuration are shown in FIGS. 5-7. FIG. 5 shows a top front perspective view, FIG. 6 shows a side view, and FIG. 7 shows a cross-sectional view of the intravaginal device 500 in a collapsed configuration. In some embodiments, the intravaginal device 500 comprises a ring support 502 and a receptacle 510. In some embodiments, the ring support 502 has an outer perimeter 504. In some embodiments, the ring support 502 comprises one or more flexible areas 506. In some embodiments, the one or more flexible areas 506 allow the ring support 502 to bend when a force is applied to the ring support 502. In some embodiments, the receptacle 510 comprising a top rim 512, a base 514, and a wall 516 connecting the base to the top rim. In some embodiments, the outer perimeter 504 may be larger by at least 10% than an outer perimeter of the top rim 512. In some embodiments, the top rim 512 comprises an opening 208. In some embodiments, the ring support 502 has a width larger than a thickness of the wall 516 of the receptacle 510. In some embodiments, the wall 516 of the receptacle 510 comprises two or more foldable areas 518, 520. In some embodiments, each of the two or more foldable areas 518, 520 comprise a notched circumference along the wall that is substantially parallel to the top rim. In some embodiments, the wall 516 of the receptacle 510 is collapsible. In some embodiments, the wall 516 of the receptacle 510 has a height that is no more than a height of the ring support 502 when the wall 516 is collapsed. In some embodiments, the two or more foldable areas 518, 520 are configured to fold the wall of the receptacle in alternating directions. In some embodiments, a first notched circumference of a first of the two or more foldable areas is notched on an outer surface of the wall and a second notched circumference of a second of the two or more foldable areas is notched on an inner surface the wall. Although collapsed, closed configurations of the collapsible intravaginal cup devices and their uses for collecting menstrual fluids are discussed above with respect to FIGS. 5-7, any of a variety of intravaginal cup devices having various closed configurations as appropriate to the requirements for collecting intravaginal fluids or providing support to the pelvic organs may be utilized in accordance with embodiments of the invention.

In some embodiments, the receptacle 104, 210, 510 of the intravaginal cup device 102, 200, 500 may collect menstrual fluid when inserted into the vaginal canal in an open configuration. In some embodiments, the receptacle comprises a main body that is tapered from the top rim to the base. In some embodiments, the main body of the receptacle may have a conical shape. In some embodiments, the main body of the receptacle may have a bowl shape. In some embodiments, the outer perimeter of the top rim is greater than an outer of the base. In some embodiments, the receptacle comprises an opening at the top rim and closed base. In some embodiments, the main body of the receptacle, also referred herein as the wall of the receptacle, may form a cavity that is configured to collect fluids in an open configuration.

In some embodiments, the receptacle 104, 210, 510 may be made from one or more biocompatible elastomeric materials. In some embodiments, the receptacle may be made completely of the biocompatible elastomeric material. In some embodiments, the biocompatible elastomeric material may be soft and compressible. In some embodiments, the material comprises medical grade silicone rubber. In some embodiments, the material may have mechanical resilience to restore to its original shape.

In some embodiments, the opening of the receptacle 104, 210, 510 may be reinforced by the ring support 106, 202, 502. In some embodiments, the ring support comprises a solid material covered with a biocompatible elastomeric material. In some embodiments, the solid material comprises a biocompatible material, including but not limited to plastics, metals, or polymers. In some embodiments, the ring support may function similarly to a pessary by exerting gentle pressure on the vaginal wall. In some embodiments, the outer perimeter of the ring support may apply pressure to a vaginal wall once inserted into a vaginal canal. In some embodiments, the outer perimeter of the ring support may distend the vaginal wall once inserted into the vaginal canal. In some embodiments, the pressure on the vaginal wall may help to support the anteriorly located urethra. In some embodiments, the pressure on the vaginal wall may help to support the posteriorly located rectum. In some embodiments, the pressure on the vaginal wall may help to reduce symptoms of pelvic organ prolapse and/or urinary/fecal incontinence. In some embodiments, the pressure on the vaginal wall and the urethra may help to reduce symptoms of urinary incontinence. In some embodiments, the pressure on the vaginal wall and the rectum may help to reduce symptoms of fecal incontinence.

In some embodiments, the ring support 106, 202, 502 comprises one or more flexible areas 206, 506 that are more flexible than rest of the ring support. In some embodiments, the ring support may be configured to be bendable at or adjacent to the one or more flexible areas. In some embodiments, the one or more flexible areas may have a higher elasticity than rest of the ring support. In some embodiments, the one or more flexible areas of the ring support may act an internal hinge that allows the device to fold along its central axis for insertion. In some embodiments, folding along its central axis of the ring support may result in the ring support folding in one direction only. In some embodiments, the device may bend only in one direction. In some embodiments, the device may bend in two directions. In some embodiments, the device may bend in more than two directions. In some embodiments, the device may bend to form a V-shape on a side view of the device. In some embodiments, the pressure applied by the user may bend the device lengthwise. In some embodiments, the ring support comprises one or more internal hinges that allows the device to fold along its central axis for insertion.

In some embodiments, the one or more flexible areas 206, 506 may be thinner than the rest of the ring support to be more flexible. In some embodiments, the one or more flexible areas may be treated by heat, a chemical, or mechanical force, or a combination thereof to create the flexible areas. In some the one or more flexible areas is made of the same material than rest of the ring support. In some the one or more flexible areas comprises one or more different materials than rest of the ring support.

In some embodiments, the one or more flexible areas 206, 506 may be thinner than the rest of the ring support 202, 502 to be more flexible. In some embodiments, the one or more flexible areas may be thinner than the rest of the ring support by at least 5%, 10%, 15%, 20%, 25%, 30%, 35%, 40%, 45%, or 50%. In some embodiments, the one or more flexible areas may be thinner than the rest of the ring support by no more than 10%, 15%, 20%, 25%, 30%, 35%, 40%, 45%, or 50% in thickness. In some embodiments, the one or more flexible areas may be thinner than the rest of the ring support by about 5%, 10%, 15%, 20%, 25%, 30%, 35%, 40%, 45%, or 50% in thickness. In some embodiments, the one or more flexible areas may be thinner than the rest of the ring support by at least 1 mm, 2 mm, 3 mm, 4 mm, 5 mm, 6 mm, 7 mm, 8 mm, 9 mm, 10 mm, 15 mm, 20 mm, 25 mm, 30 mm, 35 mm, 40 mm, 45 mm, or 50 mm. In some embodiments, the one or more flexible areas may be thinner than the rest of the ring support by no more than 5 mm, 10 mm, 15 mm, 20 mm, 25 mm, 25 mm, 30 mm, 35 mm, 40 mm, 45 mm, or 50 mm. In some embodiments, the one or more flexible areas may be thinner than the rest of the ring support by about 1 mm, 2 mm, 3 mm, 4 mm, 5 mm, 6 mm, 7 mm, 8 mm, 9 mm, 10 mm, 15 mm, 20 mm, 25 mm, 30 mm, 35 mm, 40 mm, 45 mm, or 50 mm.

In some embodiments, the intravaginal cup device 102, 200, 500 comprises a biocompatible material. In some embodiments, the biocompatible material comprises a biocompatible polymer. In some embodiments, the biocompatible polymer may be a biocompatible elastomeric polymer. In some embodiments, the intravaginal cup device may be covered with the biocompatible polymer. In some embodiments, the intravaginal cup device may be entirely covered with the biocompatible polymer. In some embodiments, the intravaginal cup device may be partially covered with the biocompatible polymer. In some embodiments, the biocompatible elastomeric polymer comprises silicone, polyurethane, polydimethylsiloxane (PDMS), thermoplastic elastomers, polyolefin elastomers, polydiene elastomers, poly(vinyl chloride), nitrile, natural rubber, hydrogels, or combinations thereof. In some embodiments, the biocompatible elastomeric polymer comprises silicone. In some embodiments, the biocompatible elastomeric polymer is silicone. In some embodiments, the silicone is a medical-grade silicone. In some embodiments, the biocompatible elastomeric polymer may allow for the receptable to fold lengthwise along an axis running from the top rim to the base. In some embodiments, the biocompatible elastomeric polymer may allow the receptable to be compressible and collapsible. In some embodiments, the biocompatible elastomeric polymer may be compatible with one or more sterilization techniques. In some embodiments, the biocompatible elastomeric polymer may be compatible with one or more of radiation sterilization, steam sterilization, or ethylene oxide treatment sterilization. In some embodiments, the biocompatible elastomeric polymer may be soft and flexible. In some embodiments, the biocompatible elastomeric polymer may be chosen to enable the device to fold and return to its original shape before folding. In some embodiments, the biocompatible elastomeric polymer has high elasticity to allow the device to fold and return to its original shape before folding. In some embodiments, the biocompatible elastomeric polymer may be chosen to enable the receptacle to fold and return to its original shape before folding. In some embodiments, the biocompatible elastomeric polymer may have a tensile strength between 0.1 MPa to 50 MPa. In some embodiments, the biocompatible elastomeric polymer may have a tensile failure strain between 100% to 500%. In some embodiments, the biocompatible elastomeric polymer may have a tensile strength between 0.1 MPa to 20 MPa. In some embodiments, the biocompatible material of the device is suitable for repeated uses after cleaning of the device after each use.

In some embodiments, the outward surface of the wall 216, 516 of the receptacle 104, 210, 510 may be treated to provide improved grip and feel for the user. In some embodiments, the outward surface of the wall of the receptacle may have a textured surface. In some embodiments, the outward surface of the wall of the receptacle may be treated to create a textured surface. In some embodiments, the textured surface may provide improved grip of the receptacle. In some embodiments, the outward surface of the wall of the receptacle comprises one or more outward protrusions. In some embodiments, the one or more outward protrusions may provide improved grip of the receptacle. In some embodiments, the outward surface of the wall of the receptacle comprises one or more inward indentations. In some embodiments, the one or more inward indentations may provide improved grip of the receptacle. In some embodiments, the improved grip may facilitate the insertion of the device into the vaginal canal. In some embodiments, the improved grip may provide friction to keep the device in place in the vaginal canal and reduce movement of the device within the vaginal canal.

In some embodiments, the intravaginal cup devices 102, 200, 500 may have various sizes and dimensions. In some embodiments, an array of sizes of the intravaginal cup devices may be provided. In some embodiments, the sizes of the intravaginal cup devices may be tailored to the user needs, including but not limited to vagina size, degree of pelvic floor weakness, degree of organ prolapse, or volume of menstrual fluid flow.

In some embodiments, the ring support 106, 202, 502 has a circular shape. In some embodiments, the ring support has an oval shape. In some embodiments, the ring support has an irregular shape. In some embodiments, the ring support has an asymmetric shape.

In some embodiments, the ring support 106, 202, 502 has a width larger than a thickness of the wall 216, 516 of the receptacle 210, 510. In some embodiments, the ring support has a width that is larger than the thickness of the wall of receptacle by at least 1%, 2%, 3%, 4%, 5%, 6%, 7%, 8%, 9%, 10%, 15%, 20%, 25%, 30%, 35%, 40%, 45%, or 50%. In some embodiments, the ring support has a width that is larger than the thickness of the wall of receptacle by no more than 5%, 10%, 15%, 20%, 25%, 30%, 35%, 40%, 45%, or 50%. In some embodiments, the ring support has a width that is larger than the thickness of the wall of receptacle by about 1% to 50%, 5% to 40%, 10% to 40%, 15% to 40%, 20%, to 40%, 20% to 50%, or 30% to 50%. In some embodiments, the ring support has a width that is larger than the thickness of the wall of receptacle by at least 1 mm, 2 mm, 3 mm, 4 mm, 5 mm, 6 mm, 7 mm, 8 mm, 9 mm, 10 mm, 15 mm, 20 mm, 25 mm, 30 mm, 35 mm, 40 mm, 45 mm, or 50 mm. In some embodiments, the ring support has a width that is larger than the thickness of the wall of receptacle by no more than 5 mm, 10 mm, 15 mm, 20 mm, 25 mm, 30 mm, 35 mm, 40 mm, 45 mm, or 50 mm. In some embodiments, the ring support has a width that is larger than the thickness of the wall of receptacle by about 1 mm to 50 mm, 5 mm to 40 mm, 10 mm to 40 mm, 15 mm to 40 mm, 20 mm, to 40 mm, 20 mm to 50 mm, or 30 mm to 50 mm.

In some embodiments, the ring support 106, 202, 502 has a width of at least 5 mm and no more than 50 mm. In some embodiments, the width refers to the distance between the inner perimeter and the outer perimeter of the ring support. In some embodiments, the width refers to the thickness of the ring support. In some embodiments, the width of the ring support is at least 1 mm, 2 mm, 3 mm, 4 mm, 5 mm, 6 mm, 7 mm, 8 mm, 9 mm, 10 mm, 15 mm, 20 mm, 25 mm, 30 mm, 35 mm, 40 mm, 45 mm, or 50 mm. In some embodiments, the width of the ring support is no more than 5 mm, 6 mm, 7 mm, 8 mm, 9 mm, 10 mm, 15 mm, 20 mm, 25 mm, 30 mm, 35 mm, 40 mm, 45 mm, or 50 mm. In some embodiments, the width of the ring support is about 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 25 mm, 30 mm, 35 mm, 40 mm, 45 mm, or 50 mm. In some embodiments, the ring support has a width of 1 mm to 50 mm, 5 mm to 50 mm, 5 mm to 40 mm, 5 mm to 30 mm, 5 mm to 20 mm, or 5 mm to 10 mm. In some embodiments, the width of the ring support is about 12.4 mm.

In some embodiments, the ring support 106, 202, 502 has a height of at least 5 mm and no more than 50 mm. In some embodiments, the height refers to the distance between the top and the bottom of the ring support. In some embodiments, the height refers to the thickness of the ring support. In some embodiments, the height of the ring support is at least 1 mm, 2 mm, 3 mm, 4 mm, 5 mm, 6 mm, 7 mm, 8 mm, 9 mm, 10 mm, 15 mm, 20 mm, 25 mm, 30 mm, 35 mm, 40 mm, 45 mm, or 50 mm. In some embodiments, the height of the ring support is no more than 5 mm, 6 mm, 7 mm, 8 mm, 9 mm, 10 mm, 15 mm, 20 mm, 25 mm, 30 mm, 35 mm, 40 mm, 45 mm, or 50 mm. In some embodiments, the height of the ring support is about 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 25 mm, 30 mm, 35 mm, 40 mm, 45 mm, or 50 mm. In some embodiments, the ring support has a height of 1 mm to 50 mm, 5 mm to 50 mm, 5 mm to 40 mm, 5 mm to 30 mm, 5 mm to 20 mm, or 5 mm to 10 mm. In some embodiments, the height of the ring support is about 12.4 mm. In some embodiments, the height and the width of the ring support are the same. In some embodiments, the height and the width of the ring support are different.

In some embodiments, the ring support 106, 202, 502 has a diameter of at least 5 mm and no more than 100 mm. In some embodiments, the diameter refers to the longest distance between a midpoint of between the inner and the outer perimeter of the ring support and a second midpoint between the inner and the outer perimeter of the ring support. In some embodiments, the diameter of the ring support is at least 10 mm, 15 mm, 20 mm, 25 mm, 30 mm, 35 mm, 40 mm, 45 mm, 50 mm, 55 mm, 60 mm, 65 mm, 70 mm, 80 mm, 85 mm, 90 mm, 95 mm, or 100 mm. In some embodiments, the diameter of the ring support is no more than 20 mm, 25 mm, 30 mm, 35 mm, 40 mm, 45 mm, 50 mm, 55 mm, 60 mm, 65 mm, 70 mm, 80 mm, 85 mm, 90 mm, 95 mm, or 100 mm. In some embodiments, the diameter of the ring support is about 10 mm, 11 mm, 12 mm, 13 mm, 14 mm, 15 mm, 16 mm, 17 mm, 18 mm, 19 mm, 20 mm, 25 mm, 30 mm, 35 mm, 40 mm, 45 mm, 50 mm, 51 mm, 52 mm, 53 mm, 54 mm, 55 mm, 56 mm, 57 mm, 58 mm, 59 mm, 60 mm, 65 mm, 70 mm, 80 mm, 85 mm, 90 mm, 95 mm, or 100 mm. In some embodiments, the diameter of the ring support is about 56 mm.

In some embodiments, the intravaginal cup device has a diameter of the opening 208 of the receptacle 210 of at least 5 mm and no more than 100 mm. In some embodiments, the diameter refers to the longest distance of the top rim of the receptacle. In some embodiments, the diameter of the opening is at least 10 mm, 15 mm, 20 mm, 25 mm, 30 mm, 35 mm, 40 mm, 45 mm, 50 mm, 55 mm, 60 mm, 65 mm, 70 mm, 80 mm, 85 mm, 90 mm, 95 mm, or 100 mm. In some embodiments, the diameter of the opening is no more than 20 mm, 25 mm, 30 mm, 35 mm, 40 mm, 45 mm, 50 mm, 55 mm, 60 mm, 65 mm, 70 mm, 80 mm, 85 mm, 90 mm, 95 mm, or 100 mm. In some embodiments, the diameter of the opening is about 10 mm, 11 mm, 12 mm, 13 mm, 14 mm, 15 mm, 16 mm, 17 mm, 18 mm, 19 mm, 20 mm, 25 mm, 30 mm, 35 mm, 40 mm, 45 mm, 50 mm, 51 mm, 52 mm, 53 mm, 54 mm, 55 mm, 56 mm, 57 mm, 58 mm, 59 mm, 60 mm, 65 mm, 70 mm, 80 mm, 85 mm, 90 mm, 95 mm, or 100 mm. In some embodiments, the diameter of the opening is about 56 mm.

In some embodiments, the receptable 210 in the open, expanded configuration has a height. In some embodiments, the height of the receptacle in the open, expanded configuration is measured from the top rim to the base of the receptacle. In some embodiments, the height of the receptable in the open, expanded configuration is at least 5 mm, 10 mm, 15 mm, 20 mm, 25 mm, 30 mm, 35 mm, 40 mm, 45 mm, or 50 mm. In some embodiments, the height of the receptable in the open, expanded configuration is no more than 10 mm, 15 mm, 20 mm, 25 mm, 30 mm, 35 mm, 40 mm, 45 mm, 50 mm, 55 mm, 60 mm, 65 mm, 70 mm, 80 mm, 85 mm, 90 mm, 95 mm, or 100 mm. In some embodiments, the height of the receptacle in the open, expanded configuration is about 10 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 40 mm, 45 mm, 50 mm, 51 mm, 52 mm, 53 mm, 54 mm, 55 mm, 56 mm, 57 mm, 58 mm, 59 mm, 60 mm, 65 mm, 70 mm, 80 mm, 85 mm, 90 mm, 95 mm, or 100 mm. In some embodiments, the height of the receptable in the open, expanded configuration is about 27 mm.

The receptacle 210 may hold a volume of fluid in the open configuration. In some embodiments, the receptacle in the open configuration may hold between 1 ml to 100 ml, 5 ml to 75 ml, 5 ml to 50 ml, 10 ml to 75 ml, 10 to 50 ml of fluid.

In some embodiments, the two or more foldable areas of the wall of the receptable for folding the receptacle in to the collapsed configuration are spaced at least 0.5 mm, 1 mm, 2 mm, 3 mm, 4 mm, 5 mm, 6 mm, 7 mm, 8 mm, 9 mm, 10 mm, or 15 mm apart from each other. In some embodiments, the two or more foldable areas of the wall of the receptable are spaced no more than 1 mm, 2 mm, 3 mm, 4 mm, 5 mm, 6 mm, 7 mm, 8 mm, 9 mm, 10 mm, or 15 mm apart from each other. In some embodiments, the two or more foldable areas of the wall of the receptable are spaced about 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, or 15 mm apart from each other. In some embodiments, the two or more foldable areas of the wall of the receptable may allow for 2, 3, 4, 5, 6, 7, 8, 9, or 10 folds of the wall of the receptacle. In some embodiments, the two or more foldable areas of the wall of the receptable may allow for 4 folds of the wall of the receptacle.

Although specific components of intravaginal cup devices are discussed above, various components of intravaginal cup devices including, but not limited to, intravaginal cup devices with ring support, receptacles, and polymers as appropriate to the requirements of a specific application can be utilized in accordance with embodiments of the invention. Methods of using intravaginal cup devices in accordance with embodiments of the invention are discussed further below.

Methods of Using Intravaginal Cup Devices

Provided herein are methods of using the intravaginal cup devices 102, 200, 500, also referred herein as intravaginal insert devices, intravaginal support devices, or intravaginal devices, described herein. Usually, the intravaginal cup device is inserted into the vaginal canal of the user to collect intravaginal fluid and provide support for the tissues and organs in pelvic floor. Often, the intravaginal cup device may reduce symptoms of pelvic organ prolapse and urinary and/or fecal incontinence in the user when the device is in place in the vaginal canal of the user.

In order to insert the device into a vagina, the user may grasp and apply pressure to the ring support to bend the ring support at or around the flexible areas of the ring support. In some embodiments, the user may bend the ring support by grasping as to close the ring support in half. In some embodiments, the device may bend only in one direction. In some embodiments, the one or more flexible areas of the ring support may act an internal hinge that allows the user to fold the device in a predetermined direction only. In some embodiments, the device may bend in more than two directions. In some embodiments, the device may bend to form a V-shape on a side view of the device. In some embodiments, the pressure applied by the user may bend the device lengthwise. In some embodiments, the user may place and insert the bent device into the opening of the vaginal canal. In some embodiments, the user may place the bent device into the vaginal introitus along its central axis.

In some embodiments, the device may unfold to its original form once placed inside the vagina and the pressure on the ring support from the user is released. Often, the biocompatible material of the device may be flexible and resilient to bend with pressure and return its original form once the pressure is released. In some embodiments, the unfolded device may nestle within the posterior fornix of the vagina. In some embodiments, the receptacle of the device may nestle at the posterior and inferior aspect of the vaginal canal. In some embodiments, the ring support of the device may nestle at the anterior and superior aspect of the vaginal canal. In some embodiments, the ring support functions similarly to a pessary by exerting pressure on the vaginal wall. In some embodiments, the ring support may apply pressure to the vaginal wall once inserted into the vaginal canal. In some embodiments, the ring support may distend the vaginal wall once inserted into the vaginal canal. In some embodiments, the pressure exerted on the vaginal wall by the ring support may allow the device to maintain its position within the vaginal canal. An illustration of the intravaginal cup device placed in the vaginal canal of the user is shown in FIG. 1.

In some embodiments, the receptable may be in an open configuration in the vaginal canal. In some embodiments, the receptacle may be a collapsed configuration in the vaginal canal. In some embodiments, the device may be inserted into the vagina with the receptacle in the collapsed configuration. In some embodiments, the device may be inserted into the vagina with the receptacle in the open configuration. In some embodiments, the receptable may be pulled into open configuration after the device was inserted into the vagina with the receptacle in the collapsed configuration.

With the receptacle in the expanded, open configuration, the device may be grasped at the ring-support structure and pinched lengthwise along its central axis to be inserted into the vaginal canal of the user. In some embodiments, the device may be inserted into the user's vagina with the open configuration receptacle folded along its central axis. Once the device is inserted into the vagina and the pressure on the ring support is released, the device may return to its original form where the receptacle in unfolded and the ring support is unbent. In some embodiments, the ring support may provide support to the vaginal wall to improve and prevent symptoms of pelvic floor prolapse and urinary and/or fecal incontinence. In some embodiments, the expanded, open receptacle may collect menstrual fluid and other fluids in the vaginal canal.

To remove the device, the user may pinch the edge of the ring support inward and onto itself. The pressure from the user may cause the device to fold lengthwise for ease of removal of the device. In some embodiments, to remove the device, the user may grasp an edge of the receptacle at the ring support structure and slowly pull the device from the vagina. In some embodiments, the receptacle may be emptied of its contents once removed from the body of the user. In some embodiments, the device may be cleaned and reused. In some embodiments, the user may clean the device by treating with hydrogen peroxide, exposing the device to sun, boiling, or combination thereof prior to next use. In some embodiments, the material properties of the biocompatible elastomeric material are changed minimally with treatment with hydrogen peroxide, sun, or boiling. Although specific methods of using intravaginal cup devices are discussed above, various methods of use of intravaginal cup devices as appropriate to the requirements of a specific application can be utilized in accordance with embodiments of the invention. Methods of manufacturing intravaginal cup devices in accordance with embodiments of the invention are discussed further below.

Manufacturing Intravaginal Cup Devices

Provided herein are methods of manufacturing intravaginal cup devices described herein. In some embodiments, the ring support and the receptacle may be manufactured together. In some embodiments, the ring support and the receptacle are made separately and subsequently fused together into a single device. In some embodiments, the ring support may be manufactured and subsequently be covered with a second material that extends to form the receptacle. In some embodiments, the ring support may be made of a hard material, including but not limited to silicone, plastic, a biocompatible polymer.

The intravaginal cup devices may be manufactured by one or more processes suitable for a biocompatible elastomeric polymer. In some embodiments, the devices may be manufactured by one or more of 3D printing, extrusion, injection molding, liquid injection molding, compression molding, thermoforming, calendering, transfer molding, dipping, or coating.

The outer wall of the receptacle may be treated to improve the grip of the surface. In some embodiments, the outer wall of the receptacle may be formed to have protrusions or indentations as the receptacle is formed. In some embodiments, the outer wall of the receptacle may be treated to texturize the outer wall.

In some embodiments, the intravaginal cup devices may be sterilized prior to first use. In some embodiments, the intravaginal cup devices may be sterilized before packaging the device. In some embodiments, the sterilization does not materially affect the mechanical properties of the biocompatible elastomeric material of the device. In some embodiments, the sterilization does not materially affect the elastic properties of the biocompatible elastomeric material of the device.

In some embodiments, the intravaginal cup devices may be coated with a drug or a pharmaceutical agent. In some embodiments, the outer surface of the intravaginal cup devices may be impregnated with a drug or a pharmaceutical agent.

Although specific methods of manufacturing of intravaginal cup devices are discussed above, various methods of manufacturing of intravaginal cup devices as appropriate to the requirements of a specific application can be utilized in accordance with embodiments of the invention. While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. An intravaginal insert device for collecting menstrual fluid, the device comprising:
    a receptacle comprising a top rim, a base, and a wall connecting the base to the top rim, wherein the top rim comprises an opening;
    a ring support connected to the top rim and having an outer perimeter that is larger by at least 10% than an outer perimeter of the top rim;
    wherein the wall of the receptacle comprises two or more foldable areas, wherein each of the two or more foldable areas comprise a notched circumference along the wall that is substantially parallel to the top rim;
    wherein the wall of the receptacle is collapsible; and wherein the wall of the receptacle has a height that is no more than a height of the ring support when the wall is collapsed.

2. The intravaginal insert device of claim 1, wherein the ring support has a width larger than a thickness of the wall of the receptacle.

3. The intravaginal insert device of claim 1, wherein the ring support has a width of at least 5 mm and no more than 50 mm.

4. The intravaginal insert device of claim 1, wherein the ring support comprises one or more flexible areas that is more flexible than rest of the ring support.

5. The intravaginal insert device of claim 4, wherein the ring support is configured to be bendable at the one or more flexible areas.

6. The intravaginal insert device of claim 1, wherein the ring support comprises one or more flexible areas having a higher elasticity than rest of the ring support.

7. The intravaginal insert device of claim 1, wherein the outer perimeter of the ring support is configured to apply pressure to a vaginal wall once inserted into a vaginal canal.

8. The intravaginal insert device of claim 1, wherein the outer perimeter of the ring support is configured to distend a vaginal wall once inserted into a vaginal canal.

9. The intravaginal insert device of claim 1, wherein the receptacle tapers from the top rim to the base, and wherein the outer perimeter of the top rim is greater than an outer of the base.

10. The intravaginal insert device of claim 1, wherein the device comprises a biocompatible elastomeric polymer.

11. The intravaginal insert device of claim 10, wherein the biocompatible polymer comprises a medical grade silicone.

12. The intravaginal insert device of claim 1, wherein the receptacle is configured to fold lengthwise along an axis running from the top rim to the base.

13. The intravaginal insert device of claim 1, wherein the two or more foldable areas are spaced at least 1 mm apart from each other.

14. The intravaginal insert device of claim 1, wherein a first notched circumference of a first of the two or more foldable areas is notched on an outer surface of the wall and a second notched circumference of a second of the two or more foldable areas is notched on an inner surface the wall.

15. The intravaginal insert device of claim 14, wherein the two or more foldable areas are configured to fold the wall of the receptacle in alternating directions.

16. The intravaginal insert device of claim 1, wherein the wall of the receptacle comprises an outward surface comprising a surface texture, wherein the surface texture is configured to provide improved grip.

17. The intravaginal insert device of claim 1, wherein the wall of the receptacle comprises an outward surface comprising one or more outward protrusions, wherein the one or more outward protrusions are configured to provide improved grip.

* * * * *